(12) United States Patent
Smith et al.

(10) Patent No.: US 12,030,986 B2
(45) Date of Patent: Jul. 9, 2024

(54) SUSTAINED RELEASE COMPOSITION USING BIOBASED BIODEGRADABLE HYPERBRANCHED POLYESTERS

(71) Applicant: CENTRAL MICHIGAN UNIVERSITY, Mt. Pleasant, MI (US)

(72) Inventors: Patrick B. Smith, Midland, MI (US); Bobby A. Howell, Mt. Pleasant, MI (US); Cuiwei Zhang, Midland, MI (US)

(73) Assignee: CENTRAL MICHIGAN UNIVERSITY, Mt. Pleasant, MI (US)

( * ) Notice: Subject to any disclaimer, the term of this patent is extended or adjusted under 35 U.S.C. 154(b) by 0 days.

(21) Appl. No.: 16/868,339

(22) Filed: May 6, 2020

(65) Prior Publication Data
US 2020/0262974 A1  Aug. 20, 2020

Related U.S. Application Data

(63) Continuation of application No. 15/121,746, filed as application No. PCT/US2015/017069 on Feb. 23, 2015, now abandoned.

(60) Provisional application No. 61/946,599, filed on Feb. 28, 2014.

(51) Int. Cl.
| | |
|---|---|
| *A01N 25/10* | (2006.01) |
| *A01N 25/18* | (2006.01) |
| *A01N 31/14* | (2006.01) |
| *A01N 35/02* | (2006.01) |
| *A01N 37/10* | (2006.01) |
| *A61K 9/00* | (2006.01) |
| *A61K 9/70* | (2006.01) |
| *A61K 31/165* | (2006.01) |
| *A61K 31/192* | (2006.01) |
| *A61K 31/198* | (2006.01) |
| *A61K 31/573* | (2006.01) |
| *A61K 31/60* | (2006.01) |
| *A61K 47/34* | (2017.01) |
| *C08G 63/12* | (2006.01) |
| *C08G 63/91* | (2006.01) |
| *C08L 101/00* | (2006.01) |
| *C08L 101/16* | (2006.01) |

(52) U.S. Cl.
CPC .......... *C08G 63/914* (2013.01); *A01N 25/10* (2013.01); *A01N 25/18* (2013.01); *A01N 31/14* (2013.01); *A01N 35/02* (2013.01); *A01N 37/10* (2013.01); *A61K 9/0014* (2013.01); *A61K 9/7007* (2013.01); *A61K 31/165* (2013.01); *A61K 31/192* (2013.01); *A61K 31/198* (2013.01); *A61K 31/573* (2013.01); *A61K 31/60* (2013.01); *A61K 47/34* (2013.01); *C08G 63/12* (2013.01); *C08L 101/005* (2013.01); *C08L 101/16* (2013.01); *C08G 2220/00* (2013.01); *C08G 2310/00* (2013.01)

(58) Field of Classification Search
CPC .. C08G 63/914; C08G 63/12; C08G 2200/00; C08G 2310/00; A01N 25/10; A01N 25/18; A01N 31/14; A01N 35/02; A01N 37/10; A01N 31/16; A01N 37/04; A01N 37/40; A61K 9/0014; A61K 9/7007; A61K 31/165; A61K 31/192; A61K 31/198; A61K 31/573; A61K 31/60; A61K 47/34; C08L 101/005; C08L 101/16
See application file for complete search history.

(56) References Cited

U.S. PATENT DOCUMENTS

| | | | | |
|---|---|---|---|---|
| 4,734,453 A ‡ | 3/1988 | Mullins | ................... | C08F 22/22 137/13 |
| 5,136,014 A ‡ | 8/1992 | Figuly | ..................... | A61K 9/204 528/27 |
| 6,437,001 B1 ‡ | 8/2002 | Roe | .......... | A01N 35/02 |
| 6,534,600 B2 ‡ | 3/2003 | Dvornic | ............. | C08G 18/3228 525/43 |
| 6,812,298 B2 ‡ | 11/2004 | Dvornic | ............. | C08G 18/3228 525/42 |
| 8,377,917 B2 * | 2/2013 | Hersel | ..................... | A61K 47/64 514/183 |
| 2008/0207871 A1 ‡ | 8/2008 | Seiler | .................... | C08G 83/005 528/36 |

(Continued)

FOREIGN PATENT DOCUMENTS

| | | |
|---|---|---|
| WO | 9916735 A1 | 4/1999 |
| WO | WO-9916735  ‡ | 4/1999 |

(Continued)

OTHER PUBLICATIONS

Declaration by Bobby A. Howell, submitted in U.S. Appl. No. 15/121,746, signed May 8, 2018, pp. 1-4. (Year: 2018).*

(Continued)

*Primary Examiner* — Abigail Vanhorn
(74) *Attorney, Agent, or Firm* — Michael Best & Friedrich LLP

(57) ABSTRACT

The present invention provides a sustained release composition having hyperbranched polymers that are polyesters that are biobased and biodegradable, and that have at least one active ingredient, which composition delivers the active ingredient over time. These active ingredients can be a wide variety of compounds so long as they can covalently bind to the polymer or be encapsulated in the polymer in a manner that is released at the point of delivery, usually by acid hydrolysis or enzymatic bond scission.

21 Claims, No Drawings

(56) References Cited

U.S. PATENT DOCUMENTS

| | | | | |
|---|---|---|---|---|
| 2008/0274149 | A1 ‡ | 11/2008 | Seiler | A61P 43/00 514/1 |
| 2009/0011038 | A1 ‡ | 1/2009 | Seiler | A61K 9/1641 424/50 |
| 2009/0074704 | A1* | 3/2009 | Zhao | C08G 65/3314 424/78.17 |
| 2009/0214674 | A1 ‡ | 8/2009 | Barraud | A01N 59/00 424/718 |
| 2010/0048813 | A1* | 2/2010 | Clauss | C08G 63/78 524/604 |
| 2010/0272810 | A1 ‡ | 10/2010 | Hu | A61K 38/1858 424/487 |
| 2010/0297200 | A1 ‡ | 11/2010 | Schoenfisch | A61K 45/06 424/40 |
| 2011/0034422 | A1 ‡ | 2/2011 | Kannan | A61K 9/0051 514/15 |
| 2011/0159113 | A1 ‡ | 6/2011 | Adeli | A61K 33/24 424/64 |
| 2011/0217750 | A1 ‡ | 9/2011 | Pandit | C08G 83/003 435/178 |
| 2012/0053303 | A1 ‡ | 3/2012 | Djuric | A61K 9/146 525/437 |

FOREIGN PATENT DOCUMENTS

| | | | |
|---|---|---|---|
| WO | 0168082 | A1 | 9/2001 |
| WO | WO-0168082 | ‡ | 9/2001 |
| WO | 2011146484 | A2 | 11/2014 |
| WO | WO-2011146484 | ‡ | 11/2014 |

OTHER PUBLICATIONS

Preston, Sally J., et al. "Comparative analgesic and antiinflammatory properties of sodium salicylate and acetylsalicylic acid (aspirin) in rheumatoid arthritis." British journal of clinical pharmacology 27.5 (1989): 607-611. (Year: 1989).*

Rousseaux, Christel, et al. "Intestinal antiinflammatory effect of 5-aminosalicylic acid is dependent on peroxisome proliferator-activated receptor-γ." The Journal of experimental medicine 201.8 (2005): 1205-1215. (Year: 2005).*

Chandorkar, Yashoda, et al. "Cross-linked, biodegradable, cytocompatible salicylic acid based polyesters for localized, sustained delivery of salicylic acid: an in vitro study." Biomacromolecules 15.3 (2014): 863-875. (Year: 2014).*

Ma et al., "Dendritic Polymers for Theranostics," Theranostics, 2016; 6(7):930-947.‡

Irfan et al., "Encapsulation Using Hyperbranched Polymers: From Research and Technologies to Emerging Applications", Ind. Eng. Chem. Res., 2010, 49(3): 1169-1196.‡

Stumbe et al., "Hyperbranched Polyesters Based on Adipic Acid and Glycerol", Macromol. Rapid Commun., 2004, 25(9): 921-924.‡

Gallardo et al., "NSAIDs bound to methacrylic carriers: microstructural characterization and in vitro release analysis", Journal of Controlled Release, 2001, 71(1): 127-140.‡

Wada et al., "Locally delivered salicylic acid from a poly(anhydride-ester): Impact on diabetic bone regeneration", J. Controlled Release, 2013, 171(1): 33-37.‡

Kulshrestha et al., "Synthesis and characterization of branched polymers from lipase-catalyzed trimethylolpropane copolymerizations", Biomacromolecules, 2007, 8, 1794-1801.‡

Kafouris et al., "Biosourced Amphiphilic Degradable Elastomers of Poly(glycerol sebacate): Synthesis and Network and Oligomer Characterization", Macromolecules, 2013, 46(3): 622-630.‡

Coneski et al., "Degradable Nitric Oxide-Releasing Biomaterials via Post-Polymerization Functionalization of Cross-Linked Polyesters", Biomacromolecules, 2010, 11(11): 3208-3215.‡

Dvornic et al., "Hyperbranched Silicon-Containing Polymers via Bimolecular Non-linear Polymerization", Silicon-Containing Dendritic Polymers, Springer, 2009, 401-420.‡

Borovac et al., "Release of ibuprofen from beads for embolization: In vitro and in vivo studies", J. Controlled Release, 2006, 115(3): 266-274.‡

Mizrahi et al., "Anhydride Prodrug of Ibuprofen and Acrylic Polymers", AAPS PharmSciTech., 2009, 10(2): 453-458.‡

Li et al., "Synthesis, characterization and properties of biocompatible poly(glycerol sebacate) pre-polymer and gel", Polym. Int., 2013, 62(4): 534-547.‡

International Search Report and Written Opinion for Application No. PCT/US2015/017069 dated Aug. 11, 2015.‡

International Preliminary Report on Patentability for Application No. PCT/US2015/017069 dated Sep. 15, 2016.‡

Wyatt, "Lewis Acid-Catalyzed Synthesis of Hyperbranched Polymers Based on Glycerol and Diacids in Toluene", J Am Oil Chem Soc., 2012, 89: 313-319.‡

Wyatt et al., "Degree of Branching in Hyperbranched Poly(glycerol-co-diacid)s Synthesized in Toluene", Polymers, 2012, 4(1): 396-407.‡

Carnahan et al., Macromolecules, 39, pp. 609-616. (Year: 2006).‡

Dvornic et al., "Chapter 16 Hyperbranched Silicon-Containing Polymers via Bimolecualr Non-linear Polymerization." Silicon-Containing Dendritic Polymers, P.R. Dvornic and M.J. Owen (eds.), Springer Science + Business Media B.V., p. 401-419. (Year: 2009).‡

International Preliminary on Patentability for Application No. PCT/US2015/017069 dated Sep. 15, 2016.

Zhang, et al., "Controlled Synthesis of Hyperbranched Poly(ester)s From Biorenewable Monomers for the Delivery of Therapeutic Agents," Global Journal of Engineering Sciences, 2019, vol. 3, Issue 1, 9 pages.

Zhang, et al., "Hyperbranched poly(ester)s for delivery of small molecule therapeutics," Polymers Advanced Technologies, 2018, 29:2352-2363.

Zhang et al., "Rational Synthesis of Hyperbranched Poly(ester)s," I&EC Rsearch, 2017, pp. 1661-1670.

Zhang, et al., "Synthesis and characterization of glycerol-adipic acid hyperbranched polyesters," Polymer, 2014, pp. 5065-5072.

* cited by examiner
‡ imported from a related application

SUSTAINED RELEASE COMPOSITION USING BIOBASED BIODEGRADABLE HYPERBRANCHED POLYESTERS

CROSS-REFERENCE TO RELATED APPLICATION(S)

This is a continuation of U.S. patent application Ser. No. 15/121,746, filed Aug. 25, 2016, which is a U.S. national stage entry of International Patent Application No. PCT/US2015/017069, filed on Feb. 23, 2015, which claims priority to U.S. Provisional Patent Application No. 61/946,599, filed on Feb. 28, 2014.

FIELD OF THE INVENTION

This invention concerns the controlled delivery of active ingredients, over time, using biobased, biodegradable hyperbranched polyesters.

BACKGROUND OF THE INVENTION

Today with the concerns about recycling of plastics many manufactures would like a plastic to be biobased and biodegradable. Various approaches have been tried with varying degrees of success for recycling, efficacy and customer acceptance.

Polyesters can be synthesized from readily renewable hydroxy acid building blocks such as lactic acid and 3-hydroxybutyric acid or via poly-condensation reactions between dicarboxylic acids with diols, transesterification of diesters with diols, and ring opening polymerization of lactones. Polyesters from renewable feedstocks are very often also biodegradable, through either hydrolytic or enzymatic depolymerization to fragments which are microbially consumed. Polyesters with functional groups along their chains or in pendant groups are attracting increased interest since these groups can be used to regulate polymer material properties. Thus using polyesters from renewable sources is a desired goal for delivery systems.

Delivery Systems

Traditionally, active ingredients that are drugs have primarily consisted of small molecules that are dispensed orally (as solid pills and liquids) or as injectables. Over the past three decades, however, sustained release formulations (i.e., compositions that control the rate of drug delivery and allow delivery of the therapeutic agent at the site where it is needed) have become increasingly common and complex. Nevertheless, many questions and challenges regarding the development of new treatments as well as the mechanisms with which to administer them remain to be addressed.

Although considerable research efforts in this area have led to significant advances, drug delivery methods/systems that have been developed over the years and are currently used still exhibit specific problems that require some investigating. For example, many drugs exhibit limited or otherwise reduced potencies and therapeutic effects because they are generally subject to partial degradation before they reach a desired target in the body. Some drugs presently used in sustained delivery systems are naproxen and ibuprofen, but there are many others.

Once administered, sustained release medications deliver treatment continuously, e.g. for days or weeks, rather than for a short period of time (hours or minutes). Furthermore, orally administered therapeutics are generally preferable over injectable medications, which are often more expensive and more challenging to administer, and thus it would be highly desirable if injectable medications could simply be dosed orally. However, this goal cannot be achieved until methods are developed to safely shepherd drugs through tissue barriers, such as epithelial or dermal barriers, or specific areas of the body, such as the stomach, where low pH can degrade or destroy a medication, or through an area where healthy tissue might be adversely affected.

One objective in the field of drug delivery systems, therefore, is to deliver medications intact to specifically targeted areas of the body through a system that can control the rate and time of administration of the therapeutic agent by means of either a physiological or chemical trigger. Over the past decade, materials such as polymeric microspheres, polymer micelles, soluble polymers and hydrogel-type materials have been shown to be effective in enhancing drug targeting specificity, lowering systemic drug toxicity, improving treatment absorption rates, and providing protection for pharmaceuticals against biochemical degradation, and thus have shown potential for use in biomedical applications, particularly as components of drug delivery devices.

There is considerable published literature on the time-release delivery of medications using synthetic polymers to which medications are covalently bonded. Polymers such as acrylics (Mizrahi, B.; Domb, A., *AAPS PharmSciTech*, 2009, 10, 453-458), methacrylics (Gallardo, A.; et al., *J. Controlled Release*, 2001, 71, 127-140) and poly(vinylalcohol) (Borovac, T., et al., *J. Controlled Release*, 2006, 115, 266-274) have been investigated. There are several drawbacks to this approach, including the fact: that the synthetic polymers are not readily bioresorbable or biodegradable potentially causing adverse effects, that it is difficult to covalently bond high concentrations of actives to them, and that they often require difficult chemical syntheses. Uhrich, et al. took a different approach, synthesizing "prodrugs" where the medication itself is a part of the polymer backbone (Wada, K., et al., *J. Controlled Release*, 2013, 171, 33-37). One example of such a formulation is polyaspirin where salicylic acid was polymerized with sebacic acid to obtain a polyanhydride ester. The polymer would degrade, through hydrolysis in the stomach, releasing aspirin and sebacic acid in a time-release manner. Advantages of this approach include the ability to bind higher levels of the medication, e.g. 50 to 60% by weight, and the ability to completely degrade within the body, releasing the medication and benign co-products. There are also major limitations to this approach which include the fact that the synthetic chemistry is often complex with expensive reagents, and, more importantly, a multi-functional medication is necessary for polymerization. Most actives do not possess multifunctional structures capable of this type of polymerization.

Biodegradable Polymers

The design and engineering of biomedical polymers (e.g., polymers for use under physiological conditions) are generally subject to specific and stringent requirements. In particular, such polymeric materials must be compatible with the biological milieu in which they will be used, which often means that they show certain characteristics of hydrophilicity. They also have to demonstrate adequate biodegradability (i.e., they degrade to low molecular weight species). The polymer fragments are in turn metabolized in the body or excreted, leaving no trace.

Biodegradability is typically accomplished by synthesizing or using polymers that have hydrolytically unstable linkages in their backbone. The most common chemical functional groups with this characteristic are esters, anhydrides, orthoesters, and amides. Chemical hydrolysis of the hydrolytically unstable backbone is the prevailing mechanism for the polymer's degradation. Biodegradable polymers can be either natural or synthetic.

Synthetic polymers commonly used in medical applications and biomedical research include polyethyleneglycol (pharmacokinetics and immune response modifier), polyvinyl alcohol (drug carrier), and poly(hydroxypropylmethacrylamide) (drug carrier).

In addition, natural polymers are also used in biomedical applications. For instance, dextran, hydroxyethylstarch, albumin and partially hydrolyzed proteins find use in applications ranging from a plasma substitute, to radiopharmaceuticals and parenteral nutrition.

In general, synthetic polymers may offer greater advantages than natural materials because they can be tailored to give a wider range of properties and more predictable lot-to-lot uniformity than can be obtained from materials from natural sources. Synthetic polymers also represent a more reliable source of raw materials, having fewer concerns of infection or immunogenicity.

Methods of preparing polymeric materials are well known in the art. However, synthetic methods that successfully lead to the preparation of polymeric materials that exhibit adequate biocompatibility, biodegradability, hydrophilicity and minimal toxicity for biomedical use are scarce. The restricted number and variety of biopolymers currently available attest to this difficulty.

One class of synthetic polymers is the hyperbranched polymers that show promise for use in this area and, in particular, hyperbranched polyesters have shown promise for these applications. Their synthesis using bimolecular non-linear polymerization (BMNLP) is economically advantaged over other methods to prepare HBPs since the synthesis can be carried out using a simple, one-pot synthesis strategy while at the same time controlling important parameters such as end group functionality and molecular weight. The synthesis of hyperbranched polyesters is taught in U.S. Pat. Nos. 6,534,600 and 6,812,298, which processes are hereby incorporated by reference, but they have not been used in medical or biodegradable applications. Hyperbranched polyesters can be synthesized from a limited number of biobased, biodegradable monomers. These monomers must consist of alcohol and acid functionality and be multifunctional in nature, in order to create the hyperbranched architecture (see Dvornic, P. R.; Meier, D. J., *Hyperbranched Silicon-Containing Polymers by Bimolecular Non-linear Polymerization*, pp. 401-420 in *Silicon-Containing Dendritic Polymers*, Dvornic, P. R.; Owen, M. J., Eds., Springer, 2009). One embodiment is to use a trifunctional alcohol (such as glycerol) or tetrafunctional alcohol (such as pentaerythritol) and a difunctional acid (such as succinic, adipic, fumaric or sebacic acid). Each of these acids is biobased and biodegradable and has the added advantage that they are FDA approved.

Hyperbranched Polyesters (HB-PE)

Hyperbranched polyesters of glycerol and succinic or adipic acid have been reported in the literature. Stumbe and Bruchmann synthesized a glycerol, adipic acid HB-PE neat at 100° C. using dibutyltin oxide catalyst under reduced pressure (Stumbe, J.-F.; Bruchmann, B.; *Macromol. Rapid Commun.*, 2004, 25, 921-924). These authors varied the stoichiometry of the monomers and determined the molecular weight of the resulting polymer, but it was determined from end group titration that these polymers only went to about 85% degrees of polymerization. Average molecular weights above 20,000 were obtained, but gelation was also observed with some stoichiometries. The molecular weight of these polymers was controlled by viscosity. Since viscosity is a function of molecular weight, and the molecular weight in these systems is determined by both the stoichiometry of the reacting groups and the degree of polymerization, then viscosity is not a viable control parameter. It is possible to produce polymers with the same viscosity from these monomers which have very different end groups and therefore, different properties. It is also difficult to stop the polymerization at a given viscosity to attain a targeted molecular weight.

Wyatt and Strahan synthesized glycerol HB-PEs from succinic acid, from glutaric acid, and from sebacic acid (Wyatt, V. T., Strahan, G. D., *Polymers*, 2012, 4, 396-407). They used dibutyltin oxide as catalyst. They performed a complete structural analysis using NMR spectroscopy, but did not determine the molecular weight of the polymers. In a separate publication, Wyatt also ran the polymerizations as a function of stoichiometry and found that the molecular weight was a function of reaction temperature and time for the same initial monomer stoichiometry (Wyatt, V. T., *J. Am. Oil Chem. Soc.*, 2012, 89, 313-319). In fact, he found that the molecular weight of the polymer varied from 10,600 to 445,000 for a glycerol to glutaric acid molar ratio of 2:1 and suggested its origin was due to side reactions. Molecular weight control was difficult with this synthetic strategy.

Kulshrestha, et al. synthesized glycerol, adipic acid HB-PEs by enzyme catalysis using Novozyme 435 (Kulshrestha, A. S. et al., *Biomacromolecules*, 2007, 8, 1794-1801). A molecular weight of 3,700 was obtained by this method and alternate stoichiometries of glycerol to adipic acid were not investigated. Glycerol sebacic acid HB-PEs were synthesized by Kafouris, et al. in *Macromolecules*, 2013, 46, 622-630 and Li, et al. in *Polym. Int.*, 2013, 62, 534-547). No attempt to control the molecular weight of these polymers was made.

Clearly, it would be desired to find a biobased, biodegradable polymer that is synthetic, has controlled physical properties (e.g. molecular weight), can carry an active biological material, provide a mechanism for sustained release, and the residual materials could be recycled.

BRIEF SUMMARY OF THE INVENTION

This invention relates to a sustained release composition having a synthetic or natural polymer of hyperbranched polyesters that are biobased and biodegradable, which composition delivers at least one active ingredient over time. The active ingredient can be one or more of such active ingredients selected from a wide variety of compounds so long as they can covalently bind to the hyperbranched polyester or be encapsulated in the hyperbranched polyester in a manner that the active ingredient is released at the point of delivery, usually by hydrolysis or enzymatic action.

Specifically, this invention concerns a composition comprising a biobased, biodegradable hyperbranched polyester that has at least one active ingredient, either covalently bonded to or encapsulated in the hyperbranched polyester. Preferably the active ingredient has carboxylate, hydroxyl, amino, ketone, aldehyde, double- or triple-bond, or triazole groups to covalently bond to the hyperbranched polyester. More preferably the active ingredient has either carboxylate or hydroxyl groups to bond to the polyester. Additionally, some active ingredients form ketals with the hyperbranched polyester. The polyester can form networks.

The process to make these hyperbranched polyesters involves bimolecular non-linear polymerization (BMNLP) methodology. The process to form the composition (hyperbranched polyester and active ingredient) is provided later herein. Some preferred monomers used to prepare the synthetic hyperbranched polyester are glycerol and adipic acid and/or succinic acid. The composition may be formulated using known and customary inert components selected for the particular active ingredient's utility.

The active ingredient is released from the polyester or network either by hydrolysis or enzymatic bond scission when the active ingredient is covalently bound to the polyester or is released by diffusion, hydrolysis or enzymatic bond scission when the active ingredient is encapsulated in the polyester or network. The polyester linkage degrades into the starting monomers or other environmentally benign degradation products and the active ingredient is released and is effective. All monomers and polymeric components and biodegradation catalysts used for this sustained release system are biodegradable.

DETAILED DESCRIPTION OF THE INVENTION

Glossary

It is understood that the terminology used herein is for the purpose of describing particular embodiments only and is not intended to be limiting. As used in this specification, the singular forms "a", "an", and "the" include plural referents unless the content clearly indicates otherwise. The following terms in the Glossary as used in this application are to be defined as stated below and for these terms, the singular includes the plural.

Various headings are present to aid the reader, but are not the exclusive location of all aspects of that referenced subject matter and are not to be construed as limiting the location of such discussion.

Also, certain US patents and PCT published applications have been incorporated by reference. The U.S. Provisional Appln. 61/946,599 from which this application claims priority is hereby incorporated by reference. However, the text of such patents is only incorporated by reference to the extent that no conflict exists between such text and other statements set forth herein. In the event of such conflict, then any such conflicting text in such incorporated by reference US patent or PCT application is specifically not so incorporated in this patent.

"adipic acid" or "AA" means 1,4-butanedicarboxylic acid

"AI" means active ingredient

"Brookfield" is a brand name of a well-known line of rotating spindle viscometers which are routinely referred to in applied rheology as Brookfield viscometers (www.brookfieldengineering.com).

"BBB" means biobased biodegradable

"BMNLP" means bimolecular non-linear polymerization

"bulk" polymerization means a neat reaction system devoid of solvent

"composition" means the amount of each component present in a sample, e.g., the ratio of monomers comprising the HBP, HB-PE or BBB-HB-PE as well as that of AIs associated with the polymer as further defined herein "2,4-D" means 2,4-dichlorophenoxyacetic acid "DI water" means distilled water "DMSO" means dimethylsulfoxide "excess" means that the level of one monomer's functional group composition is greater than that of the other monomer in the BB-HB-PE or HB-PE "formulation" means a composition that has suitable known inert ingredients, and acid or enzyme, as needed as defined herein, to aid administration of the composition for the AI's intended use "g" means grams "glycerol" means 1,2,3-propanetriol "HBP" means hyperbranched polymer(s)

"HB-PE" means hyperbranched polyester polymers; this is a specific class of dendritic polymer and excludes dendrimers, dendrons, and dendrigrafts "GRAS" means generally recognized as safe by the US FDA under C.F.R. 21, Part 182

"hr" means hour(s)

"L" means liter

"min" means minute(s)

"mL" means milliliter

"$M_n$" means number average molecular weight

"$M_w$" means weight average molecular weight

"$M_z$" means z average molecular weight

"NAA" means 1-naphthylene acetic acid

"NMR" means Nuclear Magnetic Resonance using either a Varian Mercury 500 or Bruker Avance 300 spectrometer using trimethylsilane as the internal reference and measured for proton ($^1$H) and carbon ($^{13}$C)

"overnight" means from about 12 to about 14 hrs

"PDI" means polydispersity index; PDI=$M_w/M_n$

"SEC" means Size Exclusion Chromatography Molecular weights measured by SEC were performed using a Waters 1525 liquid chromatography instrument equipped with two Agilent PLgel 3 µm MIXED-E columns in series and a Waters 410 refractive index detector in series with a Wyatt Technologies DAWN Heleos-II light scattering detector. The solvent was THF at a flow rate of 1 mL min$^{-1}$. The sample concentration was 5 mg mL$^{-1}$.

"succinic acid" or "SA" means butanedioic acid

"THF" means tetrahydrofuran

"TMP" means trimethylolpropane

"p-TSA" means p-toluenesulfonic acid

"UD" means 2-undecanone or methyl nonyl ketone

"wt %" means percent by weight

The hyperbranched polyester approach described herein uses simple synthesis procedures with inexpensive, GRAS-listed reagents and is capable of achieving active ingredient loadings of 35 to 40% by weight. These materials degrade hydrolytically either through enzymatic methods or through acid-catalysis to release the active ingredient, in its active form, leaving benign co-products. Use of BMNLP technology allows targeting of a given molecular weight by choice of monomer stoichiometry for a polymerization which is taken to high degree of polymerization. This approach is much easier to control the desired molecular weight and thus the properties of the HB-PE.

This invention relates to hyperbranched polyester (HB-PE) compounds, prepared as described in U.S. Pat. No. 6,812,298, incorporated herein by reference, that are prepared from biobased monomers. The HB-PE polymers of this invention are biobased and biodegradable (BBB) and referred to as BBB-HB-PE polymers. These BBB-HB-PE polymers use hyperbranched polyesters that are taught in U.S. Pat. Nos. 6,534,600 and 6,812,298, incorporated herein by reference.

The monomers for BBB-HB-PEs are selected from FDA approved materials and the BBB-HB-PE polymers are of nanoscopic sizes. These polymers can be crosslinked to form networks, films, sheets or coatings (as described on pp. 408-410 in Dvornic, P. R.; Meier, D. J., *Hyperbranched Silicon-Containing Polymers by Bimolecular Non-linear Polymerization*; and pp. 401-420 in *Silicon-Containing Dendritic Polymers*, Dvornic, P. R.; Owen, M. J., Eds., Springer, 2009). The AI is either encapsulated (with diffusion of the AI) or covalently bonded to the HB-PE scaffold so that the rate of diffusion or the rate of this bond scission coincides well with the time desired for the AI delivery.

The covalent bond can be broken upon use, such as by hydrolysis or enzymatic degradation, to release the AI. These BBB-HB-PE polymers have diverse chemistry to bind with AI, have very high end group functionality that can be used for targeted delivery, can bind or encapsulate high loadings of AI with either rapid or time-release features, and the BBB-HB-PE polymers biodegrade after use. These types of HBPEs have been shown to effectively encapsulate actives [Irfan, M., Seiler, M., *Ind. Eng. Chem. Res.,* 2010, 49, 1169-1196.]

The BBB-HB-PE polymers of the present invention are hyperbranched polyesters, which possess the inherent capability of linear polyesters to degrade into the starting monomers either by hydrolysis or enzymatic degradation.

The monomers for the BBB-HB-PE polymers are from renewable resources and the polymers biodegrade in a controlled fashion to benign products. Examples of such monomers are multi-functional alcohols such as glycerol or pentaerythritol and difunctional acids such as furandicarboxylic, succinic, adipic or sebacic acid. All these monomers are obtained from biobased feedstocks and degrade by hydrolysis or enzymatically into environmentally benign products.

The HB-PEs from glycerol and succinic or adipic acid degrade both hydrolytically and enzymatically in a matter of hours to days, typically from about 1 to about 7 days, depending on the polymer composition, polymer molecular weight, and the type of AI.

These HB-PEs can be produced from a number of different biobased multifunctional alcohols and acids. The alcohols include glycerol, pentaerythritol, sugars such as sucrose, glucose, and xylose, sugar alcohols such as sorbitol and xylitol, 1,3-propanediol, 1,4-butanediol, resorcinol and isosorbide. The chemical structures of glucose, sorbitol and glycerol are provided below to illustrate their multifunctional nature.

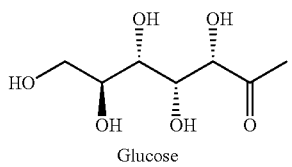
Glucose

-continued

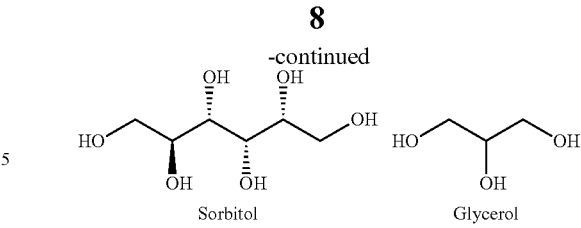

Sorbitol Glycerol

The multifunctional biobased acids include succinic, oxalic, adipic, glutaric, gluconic, sebacic, maleic, fumaric and 2,5-furandicarboxylic acid. Multifunctional biobased molecules such as tartaric acid, glucaric acid could also be used.

It has been shown that the chain length of the dicarboxylic acid monomer controls the polymer hydrophilicity and thereby the rate of degradation, providing a degree of control over the release rate of the AI and the HB-PE degradation process (see Coneski, P. N., et al., *Biomacromolecules,* 2010, 11, 3208-3215). These monomers were chosen as they have FDA approval and have been shown to slowly degrade under physiological conditions in a time frame of days. When the AI is an insect repellant, such as UD, this release rate is preferred for dermal uses to minimize skin irritation.

The BMNLP process for the preparation of BBB-HB-PE polymers involves the reaction between polyfunctional acids and alcohols. More specifically, it involves a monomer of the form $A_x$ (where A is either an OH or O(O)CR group for the polyfunctional acids; or C(O)OH, C(O)OR or C(O)Cl group for the polyfunctional alcohols), which reacts with another monomer of the form $B_y$ (where B is either a C(O)OH, C(O)OR or C(O)Cl group for the polyfunctional acids; or OH or O(O)CR group for the polyfunctional alcohols), under conditions at which neither A nor B groups can react with themselves but only with each other, and where x and y are integers where one integer is equal or larger than 2 and the other is equal or larger than 3. Additional reaction requirements are that the molar ratio of the reacting A groups and B groups (r=A/B) and the extent of the reaction must be selected so as to avoid gelation. This is accomplished in the bulk system if the extent of the reaction of the minor component (either $p_A$ or $p_B$) is equal to unity (i.e., complete conversion of the minor reagent is achieved) and the value of r is outside of the "gelation window" defined by the following equation: $1/[(x-1)(y-1)] \leq r \leq (x-1)(y-1)$.

The process to prepare these BBB-HB-PE polymers from biobased alcohols, such as excess glycerol, is shown in Scheme 1 below. In this general reaction Scheme 1, a diacid, such as adipic or succinic acid, is reacted with a multifunctional alcohol, such as glycerol. This reaction may be performed in solution or in the bulk and an acid catalyst, such as sulfuric acid or p-toluenesulfonic acid, or a polyesterification catalyst such as dibutyltin oxide or tin octoate is often used. An excess of glycerol is used in Scheme 1 which results in the HBP end groups primarily being alcohol end groups. In Scheme 1, n is 2 or 4.

Scheme 1

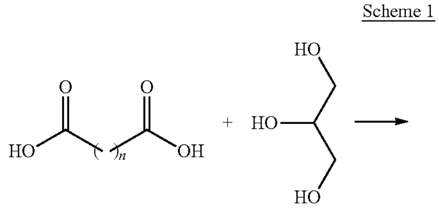

-continued
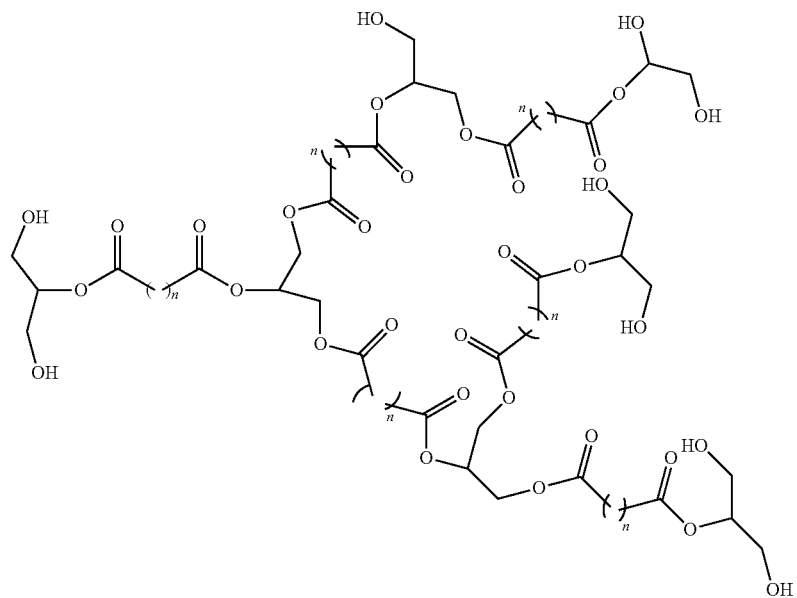
The process to prepare these BBB-HB-PE polymers from biobased acids using excess acid is shown in Scheme 2 below. The characteristics of the polymerization are similar to those described for Scheme 1 above except that the diacid is in excess resulting in a HBP possessing primarily acid end groups. In Scheme 2, n is 2 or 4.
Scheme 2
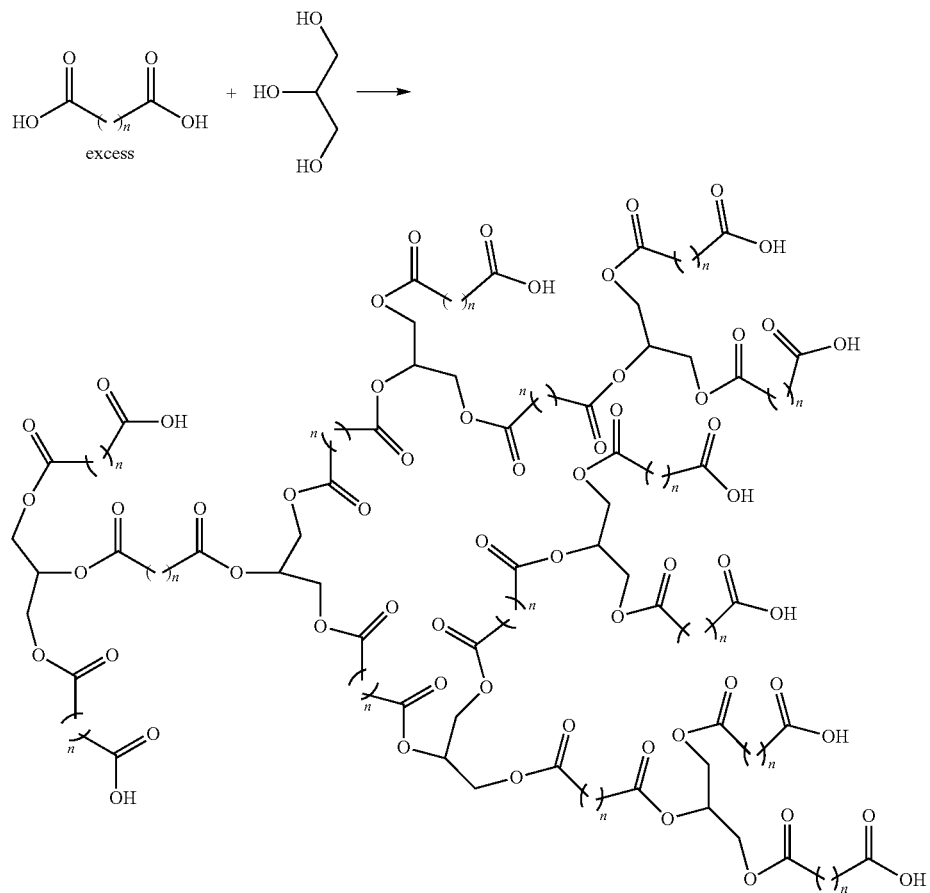

HB-PE Distribution

There is a distribution of glycerol structures in the polymer, mono-, di- and tri-ol of glycerol itself (triol) that remains in the HB-PE after the above reactions as described in Scheme 1 or 2 above. The molecular weight of the HB-PE is controlled by the BMNLP process.

One preferred BBB-HB-PE polymer is made from glycerol and (adipic acid and/or succinic acid), especially where alcohol is in excess. Other BBB-HB-PE polymers are also of interest. Various AI can be reacted as discussed below.

In some cases a ketal is formed where the ketone used is of the structure:

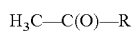

wherein: R is a $C_4$ to $C_{20}$ straight- or branched-chain alkyl, preferably $C_7$ to $C_{13}$.

Of special interest are the ketones where R is $C_9$ (UD; 2-undecanone) or $C_{13}$ (2-tridecanone). UD is an approved insect repellant.

Since there is a distribution of hydroxyl structures on the HB-PE, there is a distribution of ketal structures formed as shown below. The R-group is an adipate ester connecting the terminal glycerol unit to the HB-PE. Dioxane and dioxolane structures form as well as inter- and intra-molecular ketals. These latter ketals can be between primary alcohol groups as shown or between secondary and primary alcohols or secondary and secondary alcohols. Evidence from NMR and SEC suggests that they all form. There is also a distribution of molecular weights for the HB-PE so the resulting product is a distribution of species that can be defined statistically (molecular weight distribution) and with an average composition.

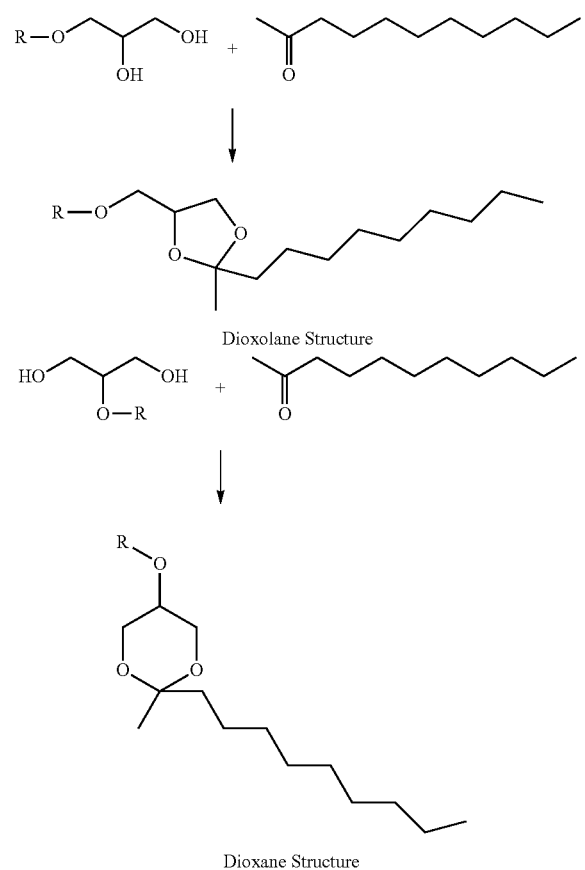

Intermolecular Ketal Structure

Bonding of BBB-HB-PE with AI

The present BBB-HB-PE compounds serve as delivery systems for the AI. The AI is either bonded to the BBB-HB-PE polymer through end groups by a readily cleavable bond at the site of use or is encapsulated in a host-guest complex within the BBB-HB-PE polymer. As used herein "associated with" means that the active ingredient (AI) can be physically encapsulated within the HB-PE, dispersed partially or fully throughout the HB-PE, or attached or linked to the HB-PE or any combination thereof, whereby the attachment or linkage is by means of covalent bonding, hydrogen bonding, adsorption, absorption, metallic bonding, van der Walls forces or ionic bonding, or any combination thereof. When the AI is encapsulated in the HB-PE, it can be "associated with" the HB-PE by covalent, coulombic, hydrophobic, or chelation type association between the AI and moieties located within in the HB-PE such as —OH or C(O)OH moieties.

HB-PE (a class of dendritic polymers) does not possess a defined void volume, in contrast to dendrimers which have a defined void volume (another class of dendritic polymers). BBB-HB-PE can therefore release an encapsulated AI more easily. A preferred bonding between the AI and BBB-HB-PE is an ester linkage, which can be hydrolyzed by an esterase to release the AI. These ester linkages are formed from acids and alcohols such as found as end groups in the BBB-HB-PE described in Schemes 1 and 2 above.

Carbonyls such as ketones and aldehydes can be bound with glycols such as glycerol through terminal groups on the BBB-HB-PE to form dioxolanes. The double and triple bonds of an AI can be bound by several techniques: reversible Diels Alder reaction with furan end groups on the BBB-HB-PE; click chemistry with triazole end groups on the BBB-HB-PE; or Michael addition with amine end groups on the BBB-HB-PE. Especially preferred are those AIs that have carboxylate, hydroxyl or amine groups to covalently bond to the BBB-HB-PE. As will be appreciated, many such AI exist. Some AIs that are possible include insect repellants such as 2-undecanone, and 2-tridecanone; plant hormones such as 1-naphthalene acetic acid and auxin; herbicides such as glyphosate (Roundup®, trademark of Monsanto) and 2,4-D; NSAIDs such as naproxen and ibuprofen; the anti-acne drug salicylic acid; antibiotics such as the penicillin and related antibiotics, gentamycin, and neomycin; anti-inflammatories such as hydrocortisone; antifungals such as fluconazole; disinfectants such as ticlosan; analgesics such as capsaicin; transdermal drugs such as testosterone; vitamins such as vitamin A and vitamin D; veterinary drugs such as diclofenac, nystatin, surolan, and liothyronine; and many others. The chemical structures of several of these compounds are given below showing their amine, carboxylic acid and hydroxyl reactive functional groups through which they can be covalently bonded to the BBBV-HB-PE for controlled delivery.

Core structure for penicillin-related antibiotics

Gentamicin

Hydrocortisone

Vitamin A

Fluconazole

Nystatin

Testosterone

Triclosan

BBB-HB-PE Release of AI

For the AI to release from the BBB-HB-PE polymer, the covalent bonds with the BBB-HB-PE are broken by hydrolysis or enzymatic bond scission. If the AI is encapsulated in the BBB-HB-PE, it can be released over time by diffusion or by hydrolysis or enzymatic bond scission.

When hydrolysis is by an acid to cause the release of the AI from the BBB-HB-PE polymer, the $pK_a$ of the acid in the formulation or available in the environment (such as soil) is important. If a strong acid, such as HCl ($pK_a=-8$) or p-TSA ($pK_a=-2.8$) is used, the AI is released rapidly. Phytic is also a strong acid ($pK_a=1.8$) and has 6 phosphate groups where each first proton of each ester group has that $pK_a$ of 1.8. Other suitable acids are: oxalic ($pK_a=1.2$), taurine ($pK_a=1.5$), pyruvic (2.4), alanine ($pK_a=2.3$), methlyglycine ($pK_a=2.2$), cysteic ($pK_a=1.3$), maleic ($pK_a=1.8$), aspartic ($pK_a=2.0$), threonine ($pK_a=2.1$), proline ($pK_a=2.0$), trans-4-hydroxyproline ($pK_a=1.8$), glutamic ($pK_a=2.1$), betaine ($pK_a=1.8$), picolinic acid ($pK_a=1.0$), nicotinic ($pK_a=2.2$), cis-aconitic ($pK_a=2.0$), lysine ($pK_a=2.2$), arginine ($pK_a=1.8$), phenylglycine ($pK_a=1.8$), and homocystine ($pK_a=1.6$). These acids are also biodegradable for their use as a catalyst to release AI. Thus strong acids with a $pK_a$ of from about $-8$ to about 2.2 will cause the release of the AI from the BBB-HB-PE. These strong acids catalyze the hydrolysis, including hydrolysis of the ketal, thereby releasing the AI.

To control the rate of release of AI, the following parameters can be adjusted in the formulation: 1) the level of acid catalyst present—increasing the level will increase the rate of release; 2) the $pK_a$ of the acid catalyst—the lower $pK_a$ gives faster rates; 3) the MW of the BBB-HB-PE—the lower MW will release faster; 4) the composition of the polymer—more hydrophobic monomers give slower rates; 5) the amount of water in the formulation; or 6) the temperature of the formulation. Typically, the AI is released over about 1 to about 7 days.

Formulations

Because these compositions of BBB-HB-PE compounds with AI are delivery systems, the possible uses are broad so long as the AI can be covalently bound to or encapsulated in the BBB-HB-PE. The release of the AI will depend on the application and formulation as it requires an acid or enzyme or time if by diffusion. As will be known by one skilled in the art of sustained release delivery systems, the formulations may be aqueous-based or non-aqueous or a combination and may be used as foams, gels, suspensions, emulsions, microemulsions, emulsifiable concentrates, ointments, sprays, granules, powders, and the like. These formulations may include various rheological agents, surfactants, dispersants, excipients, buffers, and other inert ingredients for the intended application and utility. The concentration of the AI in the BBB-HB-PE can be controlled by the process used to make the composition and the concentration can be measured. Thus the amount of AI for the various uses can be tuned by the polymer. If the formulation is applied to a skin surface of an animal or human, such as an insect repellant, the acid on the skin may be sufficient to begin the release of the AI from the BBB-HB-PE. Strong acid, as discussed above, can serve to catalyze the release of the AI. Such acid, as phytic acid, may be present in the soil if the formulation is used as a pesticide, fungicide or herbicide. Thus an enzyme or acid can be present in the formulation or in situ at the place of application of the formulation to promote the release of AI from the BBB-HB-PE polymer.

The formulations are applied in the usual manner for the intended utility.

Utility

Some examples of such uses are numerous and varied, including but not limited to sustained release agents for insect repellants, various agents for dermal application, for pesticides for animals and humans, and other uses and AI mentioned herein.

Wound healing often involves antibiotics and/or anti-inflammatory agents as AI, which can be delivered by the present BBB-HB-PE. The formulation is mostly oil based emollients or ointments with such AIs as gentamycin, neomycin, polymyxin B, or cortisone derivatives; preferred as a general antibiotic for wound healing are gentamycin and neomycin.

Transdermal drugs are designed to deliver therapeutic agents across the skin and may have a penetration accelerator such as DMSO used to enhance delivery. Some examples of AIs with the BBB-HB-PE for this use are scopolamine, clonidine, estradiol, estradiol/norelgestromin, ethynyl-estradiol/norelgestromin, nicotin, testosterone, lidocaine, oxybutyrin, methylphenidate, selegiline, rotigotine, and rivastigmine.

Topical drugs for dermatological or venereal diseases are formulated as tinctures, creams, or ointments. Some AIs with the BBB-HB-PE for dermatological disorders are hydrocortisone, fulconazole, capsaicin, vitamin A, and vitamin D. For venereal diseases some AIs with the BBB-HB-PE are metronidazole, nystatin, podofilox, and imiquimod. Preferred topical analgesics are capsaicin and salicylic acid; preferred topical NSAIDs are ketoprofen and ferulic acid. A topical anti-inflammatory drug is hydrocortisone derivatives.

Antibiotics are often desired to be released over time, sometimes after an initial dose as a starting treatment. Suitable as such AI with a BBB-HB-PE is, for example, penicillin, ampicillin, amoxicillin, or bacampicillin.

Antitumor agents can be released over time to treat tumors. Such agents are organo-platinum and other organo-metals known for this purpose.

Cosmetics are able to be delivered using BBB-HB-PE where the AI is used for various treatments such as oil removal or acne control where AI is aspirin, anti-inflammatory or antibiotics used as discussed for topical drugs. All these AIs can be formulated as for topical drugs discussed before.

Insecticides and herbicides that are mixed with the soil and where the AI would be withdrawn from the soil (no carryover to the next crop) contain organo-phosphates and organo-carbamates mixed with water or organic solvents to deliver to plants. If these AIs have a hydroxyl or carboxylic acid group that can form esters, they could link to the BBB-HB-PE matrix. Some AIs for insecticides are nicotine derivatives. Insect repallants are also included. Such insects are ticks, fleas, cockroaches, biting flies, mosquitoes, horse flies, deer flies, black flies, gnats, no-seeums and chiggars. UD, 2-undecanone, is approved as a mosquito repellant. This present 2-undecanone as the AI in a BBB-HB-PE degrades by hydrolysis in the presence of low levels of acid such as p-TSA, phosphoric acid, or phytic acid. Some AIs for herbicides are atrazine, 2,4-D esters, and glyphosate. A miticide AI is formic or oxalic acid.

Plant growth regulators are usually inorganic compounds or very unique structures that work at low concentrations. Some AIs for plant growth regulation are auxin, cytokinin, gibberellic acid, and naphthalene acetic acid. For example, the naphthalene acetic acid polymer degrades effectively using one of several enzymes, releasing the active, naphthalene acetic acid.

Veterinary drugs are usually special formulations of combined ingredients, often as ointments or pour-ons. Some AIs for veterinary use are Derma-Vet cream, diclofenac cream, vetropolycin, nystatin, neomycin sulfate, thiostrepton, triamcinolone acetonide, surolan drops, ivermectin pour-on, dectomax pour-on, hibitane ointment, liothyronine, and various transdermal drugs.

Disinfectants and sanitizers are used as wipes, liquids, gels, and sprays to rid a surface of microbes. Some AIs for disinfectants and sanitizers are triclosan and chlorhexidine gluconate; preferred is triclosan.

Thus this invention provides BBB-HB-PE polymers preferably made from glycerol and (adipic acid and/or succinic acid). These polymers are then reacted to covalently attach an AI that can react with either the alcohol end group or an acid end group (depending on whether the glycerol or the acid was used in excess) or the AI is encapsulated within the polymer. To release the AI over time from the polymer, various strong acids can be used, some of which are found naturally in the site for use of the BBB-HB-PE-AI, such as phytic acid in soil, or can be added to the formulation when used, or various enzymes can be present or added to the formulation. The rate of time release of the AI can be controlled by, for example, varying the level of hydrolysis catalyst in the formulation. Lower levels release the AI more slowly. Since release occurs by hydrolysis, the level of water in the formulation impacts the rate, lower levels of water causing slower release. Decreased temperature would also cause slower release. These compositions can be designed to achieve complete release of the AI in times as short as one day to times as long as several months.

The invention will be further clarified by a consideration of the following examples, which are intended to be purely exemplary of the present invention. The numbered examples are within the scope of this invention. The lettered examples are comparative.

Materials and Methods

The following general methods were used in the following examples.

$^{13}$C NMR spectroscopy of the samples was done as follows: The sample was dissolved in DMSO-d6 using a Varian Inova 500 NMR spectrometer operating at 125.7 MHz.

Size Exclusion Chromatograms (SEC) were obtained using a Waters 1525 chromatograph equipped with dRI and a Wyatt Dawn Helios II multiangle light scattering detector. The mobile phase was THF at 1 mL/min.

Two PLgel mixed E columns from Agilent were used for the separation

EXAMPLES

Example A (Comparative): Preparation of HB-PE from Trimethylolpropane (TMP) and Adipic Acid (AA)

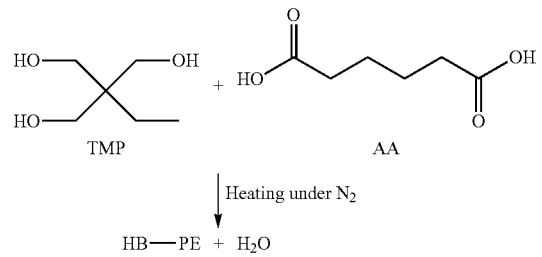

Into a dry 100 mL, three-necked, round-bottomed flask fitted with a magnetic stirring bar and a condenser bearing a gas-inlet tube, was placed 5.02 g (37.4 mmol) of trimethylolpropane (TMP), 4.08 g (27.7 mmol) of adipic acid, and 0.24 g (1.39 mmol, 2.5 mol % of the reactive carboxyl groups present) of p-TSA. The flask was mounted in an oil bath maintained at 140° C. and the mixture was stirred. The reaction was driven to completion by purging the reaction vessel with a continuous stream of nitrogen to remove water. A HB-PE of $M_w$ of 7,000-8,000 was obtained after three hrs reaction time. The product was characterized by IR, $^1$H, $^{13}$C NMR and SEC, provides the following spectra:

$^1$H NMR (500 MHz, THF-d8) δ(ppm) monomers: TMP 3.46 (s, —OCH$_2$), 1.31 (q, —CH$_2$), 0.83 (t, —CH$_3$); adipic acid (AA) 1.58 (mult., —CH$_2$), 2.22 (mult., —CH$_2$).

$^{13}$C NMR (75.5 MHz, THF-d8) δ(ppm) monomers: TMP 8.0 (—CH$_3$), 23.2 (—CH$_2$), 42.0 (—C—), 65.1 (—OCH$_2$); AA 174.5 (—C=O), 34.1 (—CH$_2$), 24.7 (—CH$_2$).

The reaction product showed expected distribution of mono-(M), di-(D) and tri-(T) functionalized molecules, the NMR assignments of which are as follows.

$^1$H NMR (500 MHz, THF-d8), δ(ppm): 4.00 (M, —OCH$_2$ ester), 3.92 (D, —OCH$_2$ ester), 3.58 (free TMP, —OCH$_2$ alcohol), 3.49 (M, —OCH$_2$ alcohol), 3.35 (D, —OCH$_2$ alcohol), 1.34 (q, —CH$_2$ free TMP), 1.23 (q, —CH$_2$ M), 1.18 (q, —CH$_2$ D), 0.78 (mult., —CH$_3$), adipate ester 2.27 (mult., —CH$_2$), 1.57 (mult., —CH$_2$).

$^{13}$C NMR (75.5 MHz, CDCl$_3$), δ(ppm): 7.6 (—CH$_3$), 22.6 (—CH$_2$), 43.0 (free TMP, —C—), 42.8 (M, —C—), 42.4 (D, —C—), 40.8 (T, —C—), 62 to 66 (—OCH$_2$), adipate ester, 174.2 (free acid, —C=O), 174.1 (M, —C=O ester), 173.7 (D, —C=O ester), 173.2 (T, —C=O ester), 34.0 (—CH$_2$), 24.6 (—CH$_2$).

SEC (in THF): $M_n$=1068, $M_w$=8600, PDI=8.1;

Refer to Example E below that provides the degradation information.

Example B (Comparative): Preparation of HB-PE from Glycerol and Adipic Acid Using p-TSA as Catalyst Synthesis of a HB-PE from glycerol and AA with p-TSA catalyst was performed by the following procedure: 5 g of glycerol, 5.95 g of AA and 0.05 g of p-TSA (0.5 wt %) were added to a 100 mL three-necked, round-bottomed flask and heated to 150° C. for about 12 hrs. The reaction mixture was blanketed with nitrogen. A clear semi-solid gel was obtained which was not soluble in any of the usual solvents for this type of polyester. This result led to the conclusion that side reactions occurred causing the HB-PE to gel.

Example 1: Preparation of BBB-HB-PE from Glycerol and Adipic Acid Using Dibutyltin Oxide as Catalyst

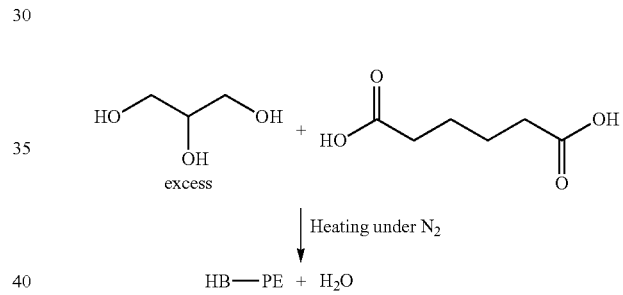

The polyester was generated by melt polymerization at 150° C. with dibutyltin oxide as catalyst and driven to completion by purging the reaction vessel with a continuous stream of nitrogen to remove water. An HB-PE of stoichiometry [—OH]/[—COOH] equal to 2.0 was achieved by using 23.8 g of AA, 20 g of glycerol and 0.219 g of dibutyltin oxide (0.5 wt %) that were added to a 250 mL three-necked, round-bottomed flask and heated to 150° C. for about 12 hrs. The reaction mixture was blanketed with nitrogen. Samples of the reaction mixture were removed periodically and analyzed according to the general procedure above.

The resulting polymer was a viscous clear colorless liquid with a degree of branching (determined from $^{13}$C NMR) of 15%-20%. The conversion was about 80% by weight. The HB-PE structure was characterized using FT-IR, NMR and SEC;

$M_w$=2,600;

$^1$H NMR (δ, DMSO-d6) 1.54 (OCOCH$_2$CH$_2$), 2.24 (OCOCH$_2$CH$_2$), 3.33-5.21 (all glycerol resonances including those of the glycerol esters and unsubstituted alcohols);

$^{13}$C NMR (δ, DMSO-d6) 23.92 (OCOCH$_2$CH$_2$), 33.17 (OCOCH$_2$CH$_2$), 59.69-65.67 (methylene carbon), 68.94-75.69 (methine carbon), 172.27-172.95 (carbonyl ester group);

IR (ATR, cm$^{-1}$) 3424 (O—H stretch), 2950, 2876 (C—H saturated), 1734 (C=O ester), 1175 (C—O stretch).

Example 2: Preparation of BBB-HB-PE from Glycerol and Succinic Acid (SA) Using Dibutyltin Oxide Catalyst

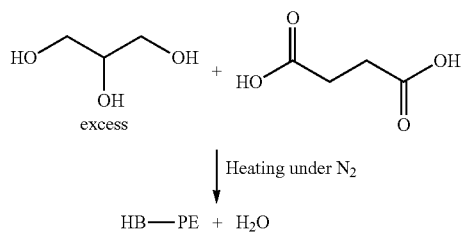

An HB-PE of stoichiometry [—OH]/[—COOH] equal to 2.0 was achieved by using 10 g of glycerol, 9.62 g of SA, and 0.098 g dibutyltin oxide (0.5 wt %) that was added to a 100 mL three-necked, round-bottomed flask and heated to 150° C. for about 12 hrs. The reaction mixture was blanketed with nitrogen. An opaque white colored semi-solid was obtained. The conversion was about 75% by weight. The HB-PE structure was characterized by FT-IR, NMR and SEC:

$M_w$=2,200;

$^1$H NMR (δ, DMSO-d6) 2.57 (OCOCH$_2$), 3.34-5.24 (all glycerol resonances including those of the glycerol esters and unsubstituted alcohols);

$^{13}$C NMR (δ, DMSO-d6) 28.51 (OCOCH$_2$), 59.37-65.82 (methylene carbon), 68.94-75.82 (methine carbon), 171.82 (carbonyl ester group);

IR (ATR, cm$^{-1}$) 3462 (O—H stretch), 2952, 2873 (C—H saturated), 1736 (C=O ester), 1175 (C—O stretch).

Example 3: Preparation of BBB-HB-PE from Glycerol and Adipic Acid (AA) Using Dibutyltin Oxide Catalyst

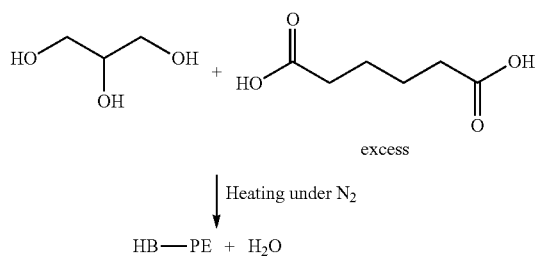

An HB-PE of stoichiometry [—COOH]/[—OH] equal to 2.0 was achieved by using 12.9 g of AA, 2.5 g of glycerol and 0.075 g of dibutyltin oxide (0.5 wt. %) that was added to a 100 mL three-necked, round-bottomed flask and heated to 150° C. for about 12 hrs. The reaction mixture was blanketed with nitrogen. The crude product was a white, opaque, waxy solid. The final product, as a solution in the minimum amount of methanol, was purified by precipitation from DI water. After purification a clear viscous liquid was obtained. The HB-PE structure was characterized using FT-IR, NMR and SEC:

$M_w$=4,000;

$^1$H NMR (δ, DMSO-d6) 1.50-1.49 (OCOCH$_2$CH$_2$), 21.7-2.2 (HOOCCH$_2$CH$_2$), 2.29 (OCOCH$_2$CH$_2$), 4.08-4.26 (all glycerol ester resonances);

$^{13}$C NMR (δ, DMSO-d6) 23.73-24.11 (OCOCH$_2$CH$_2$), 32.92-33.43 (OCOCH$_2$ CH$_2$ and HOOCCH$_2$CH$_2$), 61.88 (methylene carbon from glycerol after forming ester), 68.84 (methine carbon from glycerol after forming ester), 172.12-172.47 (carbonyl ester group), 174.45 (carbonyl acid group);

IR (ATR, cm$^{-1}$) 3225 (O—H stretch), 2953, 2873 (C—H saturated), 1739 (C=O ester), 1708 (C=O acid) 1171 (C—O stretch).

Example 4: Binding of the UD, as AI, to the BBB-HB-PE

When the alcohol end groups of the BBB-HB-PE polymer of Example 1 were reacted with UD, a ketal was formed. A majority of the hydroxyl functionality on the HB-PE polymer was converted to ketals. Because of the distribution of the hydroxyl structures on the HB-PE, there was a distribution of ketal structures formed as described above.

Part A: Ketalization of UD to HB-PE (glycerol-AA)

Into a dry 100 mL, two-necked, round-bottomed flask fitted with a magnetic stirring bar and vacuum adapter was placed 10.46 g of glycerol-AA (89.85 mmol —OH; prepared in Example 1), 7.65 g (89.85 mmol) of UD and 2 mg of p-TSA. The flask was mounted in an oil bath maintained at 120° C. and the mixture was stirred for 30 mins, after which vacuum was applied to the reaction apparatus. The reaction was continued with stirring under vacuum for 4 hrs. A viscous, clear, light yellow liquid was obtained. The conversion was about 77%. The molecular weight of the polymer increased dramatically from 2,600 of the starting HB-PE to 5,400 for the ketalized HB-PE. The $^{13}$C NMR spectrum showed a resonance from the ketal structure at about 110 ppm.

Free UD remained after the reaction for which excess of UD was used. This excess UD is beneficial in that it is potentially encapsulated by the HB-PE, providing an initial burst of protection followed by a slower time-release of UD from the HB-PE. The level of UD that can be bound to the HB-PE as a function of molecular weight (MW) is shown in Table 1 below.

TABLE 1

| Structure | MW of Polymer | UD/Molecule | MW of Polymer + UD | Wt % UD |
| --- | --- | --- | --- | --- |
| G-UD | 92 | 1 | 244 | 63 |
| G2A | 290 | 2 | 596 | 51 |
| G3A2 | 491 | 2.5 | 873.5 | 44 |
| G4A3 | 692 | 3 | 1151 | 40 |
| G5A4 | 893 | 3.5 | 1428.5 | 37 |
| G6A5 | 1094 | 4 | 1706 | 36 |
| G7A6 | 1295 | 4.5 | 1983.5 | 35 |
| G8A7 | 1496 | 5 | 2261 | 34 |
| G9A8 | 1697 | 5.5 | 2538.5 | 33 |

TABLE 1-continued

| Structure | MW of Polymer | UD/Molecule | MW of Polymer + UD | Wt % UD |
|---|---|---|---|---|
| G10A9 | 1898 | 6 | 2816 | 33 |
| G11A10 | 2099 | 6.5 | 3093.5 | 32 |
| G12A11 | 2300 | 7 | 3371 | 32 |

In Table 1, column 1 for Structure means the following:
G-UD=glycerol ketal; G2A=(glycerol)$_2$–AA; G3A2= (glycerol)$_3$–(AA)$_2$ oligomer; G4A3=(glycerol)$_4$–(AA)$_3$ oligomer; G5A4= (glycerol)$_5$–(AA)$_4$ oligomer; G6A5=(glycerol)$_6$–(AA)$_5$ oligomer; G7A6= (glycerol)$_7$–(AA)$_6$ oligomer; G8A7=(glycerol)$_8$–(AA)$_7$ oligomer; G9A8= (glycerol)$_9$–(AA)$_8$ oligomer; G10A9=(glycerol)$_{10}$–(AA)$_9$ oligomer; G11A10=(glycerol)$_{11}$–(AA)$_{10}$ oligomer; G12A11=(glycerol)$_{12}$–(AA)$_{11}$ oligomer.

These results indicate that the lower MW HB-PE polymer, about 800 to about 1,000, attach the most UD. This means G5A4 and G6A5 oligomers have a UD loading of about 36 wt %.

Part B: Ketalization of UD to HB-PE (glycerol-SA)

The synthesis of the glycerol-SA HB-PE in the neat condition produced a very viscous polymer to which UD could not be mixed even at 120° C. Therefore, the synthesis was done in solution. The HB-PE (glycerol-SA) (2 g, 19.52 mmol —OH end group) and UD (1.08 g, 9.76 mmol) with 2 mg of p-TSA in 20 mL dioxane solution were added into a 100 mL 2-necked, round-bottomed flask fitted with a magnetic stirring bar, N$_2$ inlet and outlet, a small Soxhlet extractor containing anhydrous 4 Å molecular sieves, and a condenser. The gas flow was started. The reaction mixture was heated to 120° C. and the refluxed dioxane was allowed to return to the flask through molecular sieves to remove the water by-product. The reaction mixture was stirred with heating for 5 hrs. Final product was precipitated from DI water. After drying, a viscous clear yellow liquid was obtained. The product was characterized by NMR, SEC and IR, The molecular weight of the polymer increased dramatically from 3,300 of the starting HB-PE to 5,400 for the ketalized HB-PE. The $^{13}$C NMR spectrum showed a resonance at 110 ppm consistent with a ketal structure.

Example C (Comparative): Binding of UD to the HB-PE Using Only the Residual Dibutyltin Oxide Catalyst 5.85 g (34.36 mmol) of UD and 8 g (68.72 mmol —OH) of glycerol-AA were added into a 100 mL two-necked, round-bottomed flask. The flask was mounted in an oil bath maintained at 140° C. After 5 hrs of reaction, a white viscous material was obtained. SEC chromatograms showed no evidence for the formation of any ketal, and also $^{13}$C NMR showed no ketal resonance at 110 pm.

Example 5: Binding of NAA, as AI, to the Glycerol-AA HB-PE

NAA was covalently bonded to a HB-PE with alcohol end groups using an esterification procedure similar to that with glycerol-AA of Example 1. The reaction was driven to completion by purging the reaction vessel with a continuous stream of nitrogen to remove water. The HB-PE (glycerol-AA) (2.7 g, 23.19 mmol —OH end group) and NAA (5.18 g, 27.83 mmol) with 2 mg of p-TSA were added into a 100 mL two-necked, round-bottomed flask fitted with a magnetic stirring bar. The flask was mounted in an oil bath maintained at 140° C. and the mixture was stirred for 12 hrs. The excess of NAA was removed by precipitation from mixture of ethyl acetate and hexane in 1.5:8.5 (v). A very viscous brown colored liquid was obtained. $^{13}$C NMR resonances of the carbonyl carbon of NAA at 170 to 174 ppm were consistent with e NAA ester. The NAA acid carbonyl resonance at about 177 ppm was not present after purification.

Example 6: Binding of Salicylic Acid, as AI, to BBB-HB-PE

The carboxylic acid functionality of salicylic acid was esterified with an HB-PE possessing —OH end groups. HB-PE (glycerol-AA) (10 g, 85.9 mmol —OH end group; prepared in Example 1) and salicylic acid (11.86 g, 85.9 mmol) with 20 mg of p-TSA in 140 mL triglyme solution were added into a 250 mL three-necked, round-bottomed flask fitted with a magnetic stirring bar, N$_2$ purge, a Soxhlet extractor containing 40 g of anhydrous 4 Å molecular sieves, and a condenser. The gas flow was started. The reaction mixture was heated to 150° C. and the refluxed triglyme was allowed to return to the flask through molecular sieves to remove the water by-product. The reaction mixture was stirred with heating for 12 hrs. After the reaction was complete, hexane was used to remove the triglyme solvent; the excess salicylic acid was removed by precipitation from diethyl ether. A viscous, clear yellow liquid was obtained. The product was characterized by NMR, SEC and IR. The molecular weight of the polymer increased dramatically from 1,500 of the starting HB-PE to 3,200 for the HB-PE attached to salicylic acid.

$^{13}$C NMR resonances of the carbonyl carbon of salicylic acid at 169 ppm showed that the salicylic acid ester was formed. The acid peak, around 175 ppm, was gone after purification.

Example 7: Binding of Ferulic Acid, as AI, to the BBB-HB-PE

Ferulic acid is covalently bonded to the BBB-HB-PE by esterification using the methodology of Example 5. The BBB-HB-PE of Example 1 and ferulic acid are melt esterified using p-TSA as catalyst by adding the reactants to a 100 mL two-necked, round-bottomed flask fitted with a magnetic stirring bar. The flask is mounted in an oil bath maintained at 140° C. and the mixture is stirred for 12 hrs. The reaction is driven to completion by purging the reaction vessel with a continuous stream of nitrogen to remove water. Excess ferulic acid is removed by precipitation using a solvent-nonsolvent mixture, for example ethyl acetate/hexane.

Example 8: Binding of Liothyronine, as AI, to the BBB-HB-PE

Liothyronine, a transdermal veterinary drug, has carboxylic acid functionality, and is an AI. This AI can be attached to the BBB-HB-PE with acid end groups (prepared in Example 1) in a fashion similar to that done in Example 5. It is covalently bonded to the HBP by, for example, by melt esterification using p-TSA as catalyst. The reactants are added to a 100 mL two-necked, round-bottomed flask fitted with a magnetic stirring bar. The flask is mounted in an oil bath maintained at 140° C. and the mixture is stirred for 12 hrs. The reaction is driven to completion by purging the reaction vessel with a continuous stream of nitrogen to remove water. Excess liothyronine is removed by precipitation using a solvent/non-solvent mixture, for example ethyl acetate/hexane.

Example D (Comparative)

The products of Example 1, combined with UD by the method of Example 4, were evaluated for their degradation. Lipase enzymes were ineffective in hydrolyzing the ketal and releasing UD as determined by SEC analysis.

Chemical hydrolysis with a weak acid like acetic acid ($pK_a$=4.8) was also ineffective. For example, a mixture of 1 mL of THF:glacial acetic acid in a 9:1 ratio with 0.1 mL DI water was combined with about 20 mg of HB-PE-UD. The cloudy suspension was stirred at 37° C. in a water bath for 4 days. SEC analysis of the starting materials and the degradation solution showed no change in the chromatograms indicating negligible molecular weight loss or release of 2-undecanone.

This experiment was repeated with a mixture of 1 mL buffer solution of either pH=3, 4, or 5 with a few drops of THF solvent which was combined with about 20 mg of HB-PE-UD. The cloudy suspension was stirred at 37° C. in a water bath for 4 days. SEC analysis of starting materials and degradation solution showed no discernable change in the chromatograms indicating negligible molecular weight loss or release of 2-undecanone.

Example 9: Release of AI, UD, from HB-PE

When strong acids, such as HCl ($pK_a$=−8); p-TSA ($pK_a$=−2.8) and phytic acid ($pK_a$=1.8) were used, they were very effective in releasing UD. The release rate can be varied from hours to weeks by varying the level of strong acid in the formulation. For example, when no acid is present in the formulation, UD is released over a period of months. NMR and GC-MS verified that UD was released.

Degradation experiments were conducted with a mixture of glycerol-AA-UD (from Example 4A) with glycerol in a 1:1 mole ratio, and either a 50% aqueous phytic acid solution or solid phytic acid was added. The degradation solutions were analyzed by NMR, GC-MS and SEC. The following table shows degradation data from NMR and molecular weight changes from SEC at 15% and 2% phytic acid vs. time. Release of UD was complete after 12 hrs in 15% phytic acid solution at physiological temperature (37° C.).

These data show that both temperature and the level of acid affect the degradation rate. Degradation was much faster at physiological temperature than at room temperature (about 21° C.). Degradation in 15% phytic acid was much faster than 3% phytic acid. In Table 2 the degradation conditions were about 100 mg of a composition of UD in HB-PE was mixed with glycerol in 1:1 wt ratio and phytic acid (50% water solution) was added.

TABLE 2

| Composition | % wt of phytic acid | Degradation temp (° C.) | Time (hrs) | $M_w$ (kDa) | $^{13}$C NMR data Weight Bound UD % | $^{13}$C NMR data Weight Free UD % |
|---|---|---|---|---|---|---|
| Glycerol-AA-UD | 15 | 37 | 0 | 4.7 | 11.1 | 0.0 |
| | | | 2 | 3.9 | 9.6 | 2.9 |
| | | | 4 | 3.9 | 8.5 | 3.8 |
| | | | 6 | 2.3 | 7.4 | 5.3 |
| | | | 24 | 2.1 | 0.0 | 12.2 |
| | | | 48 | 1.4 | 0.0 | 11.3 |
| | | 21 | 24 | 3.3 | 8 | 3 |
| | 2 | 37 | 2 | 4.1 | 7 | 1.2 |
| | | | 4 | 4 | 6.5 | 1.6 |
| | | | 6 | 2.7 | N/A | N/A |
| | | | 24 | 2.4 | 3.6 | 4.5 |
| | | | 48 | 2.1 | 1.8 | 5.4 |
| | | 21 | 24 | 3.7 | N/A | N/A |

Example 10: Release of NAA, as AI, from HB-PE from Glycerol and AA

The products of Example 5 were evaluated for their degradation. NAA was released both enzymatically and also with the acid catalysts of Example 9. Enzymatic degradation was much faster than acid catalyzed degradation. GC-MS and SEC verified those conclusions.

Enzymatic degradation experiments were conducted with mixture of a composition of glycerol-AA-NAA or glycerol-SA-NAA, enzymes and buffer solution (pH=5 and 7.4). Esterase from porcine liver, Lipase from Aspergillus niger, and Candida antarctica lipase B (CALB) were used in enzymatic degradation. The degradation significantly reduced the $M_w$ of the polymer and released NAA within a matter of one to two days.

Example E (Comparative): Release of NAA from a TMP-AA HB-PE

NAA was covalently bonded to the HB-PE polymer from Example A. The synthesis procedure was the same as that for binding NAA to HB-PE of glycerol-AA in Example 5. The HB-PE (TMP-AA) (3.23 g, 22.3 mmol —OH end group) and NAA (6.23 g, 33.45 mmol) were added into a 100 mL two-necked, round-bottomed flask fitted with a magnetic stirring bar. The flask was mounted in an oil bath maintained at 140° C. and the mixture was stirred for 12 hrs. The excess NAA was removed by precipitation from mixture of methanol. A very viscous, fight, yellow colored liquid was obtained. $^{13}$C NMR resonances of the carbonyl carbon of NAA at 170-173 ppm showed that NAA ester was formed, and also peaks from phenyl group at 123-134 ppm were present. The acid peak at 177 ppm was gone after purification. This material did not degrade under enzymatic conditions (enzymes used were esterase, lipase and CALB in buffer solution with pH=6.5, 7.4 and 9). SEC chromatography showed negligible molecular weight loss, and NMR confirmed insignificant release of NAA under enzymatic degradation conditions. The following table is comparative data showing the rate of polymer degradation for HB-PEs of TMP-AA and glycerol-AA. The release of NAA was confirmed by NMR and GC-MS.

Degradation conditions used in Table 3 were 2 mL of 50 mM pH=7.4 phosphate buffer solution added to about 25 mg of the composition and 2.5 mg of CALB, and stirred at physiological temperature (37° C.).

TABLE 3

| Material composition | Time (days) | Mw (kDa) |
|---|---|---|
| TMP-AA-NAA (813-49) | 0 | 7.7 |
|  | 7 | 7.5 |
|  | 28 | 7.2 |
| Glycerol-AA-NAA (856-85E) | 0 | 7.3 |
|  | 3 | 4.5 |
|  | 16 | 2.1 |

These results show that TMP-AA-NAA does not degrade and release the NAA as desired whereas glycerol-AA-NAA does release NAA.

Example 11: Production of HBPE Networks

There are a number of methods whereby HBPEs can be formed into a network such that they can be fabricated into films, sheets or coatings. For example, networks are formed when the stoichiometry of the reactants are within the gel window as taught by the BMNLP methodology. In one case, a network HBPE polymer was formed using trimethylolpropane (TMP) and adipic acid with functional group stoichiometry [—OH]/[—COOH]=1.5. BMNLP methodology teaches that this is within the gel window. Typical synthesis conditions are the following:

Into a 250-mL three-necked, round-bottomed flask equipped with a mechanical stirrer and a Soxhlet extractor filled with 40 g of 4 Å molecular sieves and fitted with a condenser bearing a gas-inlet tube, was placed a solution of 10 g (74.5 mmol TMP, 223.6 mmol of —OH) of trimethylolpropane, 10.89 g (74.5 mmol AA, 149 mmol of —COOH) of adipic acid and 0.5 g of p-TSA catalyst in 90 mL of anhydrous THF. The solution was stirred at solvent reflux with the distillate being cycled through the sieves to remove water formed as the esterification proceeded. After 20 hrs of stirring, the polymer gelled. It was a transparent, soft and rubber-like gel which was not soluble in any of the usual solvents.

Example 12: HBPE of Glycerol and Oxalic Acid

Oxalic acid was copolymerized with glycerol to yield a HBPE by the following method: 4 g of glycerol was added to a stirred three-necked, round-bottomed 100 mL flask placed in a warm water bath and 8 mL dioxane was added to dissolve the glycerol. The flask was then immersed in an ice water bath and 4.98 g of oxalyl chloride was added dropwise into the cold glycerol/dioxane solution. A nitrogen gas stream was used to purge the evolved HCl from the headspace of the vessel. The reaction was stopped after 3 hrs, the dioxane and residual HCl were roto-evaporated at 50° C. using a warm water bath. A clear viscous liquid was obtained. NMR and GPC confirmed the formation of a glycerol-oxalic acid HBPE.

The glycerol-oxalic acid HBPE was degraded in water using the following procedure: 1 mL of DI water was combined with 40 mg glycerol-oxalic acid HBPE. The cloudy suspension was stirred overnight at ambient temperature. GPC and NMR analysis showed that the HBPE degradation was complete after 20 hrs, releasing oxalic acid and glycerol.

Example 13: Binding of Triclosan, as AI, to the BBB-HB-PE

Triclosan was covalently bonded to a BBB-HB-PE with carboxylic acid endgroups using the following procedure: A solution of dicyclohexyl carbodiimide (DCC) (2.6 g, 12.6 mmol) and 1-dimethylaminopyridine (DMAP) (0.077 g, 0.63 mmol) in 100 mL of THF was cooled to 0-5° C. in an ice-water bath and the hyperbranched polyester of glycerol and adipic acid with —COOH end groups (2 g, 12.6 meq COOH) in about 20 mL of THF was added dropwise. The reaction mixture was stirred at room temperature for 12 hrs and a white precipitate formed. Triclosan (3.65 g, 12.6 mmol) in 10 mL of THF was added at room temperature with stirring and blanketed with a stream of nitrogen. The reaction mixture was then refluxed for 12 hrs. The progress of the reaction was monitored by taking aliquots at different intervals of time and analyzing them by SEC. The crude reaction mixture was purified by filtration to remove the dicyclohexylurea formed in the process, then ultrafiltration was followed to remove excess triclosan and other starting materials. The solvent in the ultrafiltration was a mixture of methylene chloride and methanol in about 1:1 ratio with the molecular weight cutoff for membrane of 1,000 Da. Purification was accomplished after 3 ultafiltration runs, followed by solvent evaporation. The viscous product was analyzed by SEC, NMR and IR. The SEC chromatogram of the resulting polymer showed that the molecular weight of the polymer was not reduced through the reaction chemistry. The $^{13}C$ NMR spectrum of the resulting polymer indicated that triclosan was esterified to the HB-PE as revealed by the O-aromatic resonances of free triclosan at 142.2, 147.5 and 150.5 ppm shifting to 142.2, 149.6 and 152.3 ppm, consistent with the triclosan ester. The acid carbonyl resonances of adipic acid also shifted upfield consistent with esterification. Side reactions involving the DCC coupling agent were also observed. This reaction was not optimized but demonstrated that it is possible to bind triclosan with this chemistry.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter. Accordingly, this description is to be construed as illustrative only and is for the purpose of teaching those skilled in the art the general manner of carrying out the invention.

What is claimed is:

1. A composition comprising:
    a) a synthetic or natural biobased, biodegradable hyperbranched polyester (HB-PE), wherein the HB-PE is derived from a reaction between glycerol and a difunctional acid having two acid groups, wherein the molar ratio of alcohol groups to acid groups is greater than or equal to 2 or less than or equal to 0.5, wherein the extent of reaction of the minor component among the glycerol and difunctional acid is about unity; and
    b) an active ingredient covalently bonded to end groups of the HB-PE;
    wherein the composition is a viscous liquid.

2. The composition of claim 1, wherein the difunctional acid is adipic acid and/or succinic acid.

3. The composition of claim 1, wherein the covalent bonding of the end groups of the HB-PE and the active ingredient is a dioxane, dioxolane, inter- or intra-molecular ketal or mixtures thereof.

4. The composition of claim 3, wherein the active ingredient is $H_3C—C(O)—R$ wherein: R is a $C_4$ to $C_{20}$ straight- or branched-chain alkyl.

5. The composition of claim 4 wherein R is $C_7$ to $C_{13}$.

6. The composition of claim 5 wherein is $C_9$ (UD; 2-undecanone) or $C_{13}$ (2-tridecanone).

7. The composition of claim 1, wherein the active ingredient is released from the HB-PE over time from about 1 day to several months.

8. The composition of claim 1, wherein the active ingredient has an amine, carboxylic acid, or hydroxyl functional group to form a covalent bond to the HB-PE.

9. The composition of claim 1, wherein the active ingredient is an agent for wound healing, dermatological disorders, or venereal disease, or is an analgesic, or an anti-inflammatory.

10. The composition of claim 9, wherein the composition is in a topical formulation.

11. The composition of claim 9, wherein the active agent is an analgesic selected from the group consisting of capsaicin, salicylic acid, ketoprofen, and ferulic acid.

12. The composition of claim 9, wherein the active agent is a hydrocortisone derivative.

13. The composition of claim 1, wherein the active ingredient is an antibiotic.

14. The composition of claim 1, wherein the active ingredient is an herbicide.

15. The composition of claim 14, wherein the herbicide is atrazine, 2,4-D esters, or glyphosate.

16. The composition of claim 1, wherein the active ingredient is a miticide.

17. The composition of claim 16, wherein the miticide is oxalic acid.

18. The composition of claim 1, wherein the active ingredient is a plant growth regulator.

19. The composition of claim 18, wherein the plant growth regulator is auxin, cytokinin, gibberellic acid, or naphthalene acetic acid.

20. The composition of claim 1, wherein the active ingredient is a disinfectant or sanitizer.

21. The composition of claim 1, wherein the active ingredient is an insect repellant.

* * * * *